United States Patent [19]

Hill

[11] 4,335,109

[45] Jun. 15, 1982

[54] WATER REPELLENT AQUEOUS WOOD TREATING SOLUTIONS

[75] Inventor: Robert E. Hill, Webster Groves, Mo.

[73] Assignee: Koppers Company, Inc., Pittsburgh, Pa.

[21] Appl. No.: 216,123

[22] Filed: Dec. 15, 1980

Related U.S. Application Data

[63] Continuation of Ser. No. 96,333, Nov. 21, 1979, abandoned.

[51] Int. Cl.$^3$ .................. A01N 59/20; A01N 59/06
[52] U.S. Cl. ................................. 424/140; 106/2; 106/15.05; 424/145; 424/146; 424/150; 424/153; 424/154; 424/289; 424/291; 424/293; 424/294; 424/295; 427/440
[58] Field of Search ............... 106/2, 15.05; 424/68, 424/140, 145, 146, 150, 153, 154, 289, 291, 293–295; 427/440

[56] References Cited

U.S. PATENT DOCUMENTS 2,571,030 10/1951 Govett et al. .................... 424/68
2,876,163 3/1959 Garizio et al. .................... 424/68

*Primary Examiner*—Lorenzo B. Hayes
*Attorney, Agent, or Firm*—Donald M. MacKay

[57] ABSTRACT

An increased water repellency is imparted to wood and other cellulosic materials with an aqueous solution containing a mixture of an aluminum halohydrate and a water soluble salt of a mono, di or trivalent cation selected from zinc, manganese, barium, calcium, cobalt, magnesium, nickel, copper, cadmium, strontium, beryllium, lead, mercury, chromium, sodium, lithium, and potassium and a monovalent anion selected from formate acetate, haloacetate, acrylate, methacrylate, propionate, chloro and bromo-propionate, butyrate, isobutyrate, nitrate, sulfamate, iodide, bromide, and chloride, said water soluble salt excluding the nitrates, sulfamates, chlorides and bromides of sodium, potassium and lithium.

2 Claims, No Drawings

WATER REPELLENT AQUEOUS WOOD TREATING SOLUTIONS

This is a continuation of application Ser. No. 096,333, filed Nov. 21, 1979, now abandoned.

SUMMARY OF THE INVENTION

This invention relates to solutions that provide increased water repellency for wood and other cellulosic materials. More particularly, the invention is related to aqueous substantially sulfate free cellulosic materials treating solutions to include suspensions, comprising a mixture of an aluminum halohydrate and a water soluble salt of a mono, di or trivalent cation selected from zinc, manganese, barium, calcium, cobalt, magnesium, nickel, copper, cadmium, strontium, beryllium, lead, mercury, chromium, sodium, lithium, and potassium, and a monovalent anion selected from formate, acetate, haloacetate, acrylate, methacrylate, propionate, chloro and bromopropionate, butyrate, isobutyrate, nitrate, sulfamate, iodide, bromide, and chloride, said water soluble salt excluding the nitrates, sulfamates, chlorides, and bromides of sodium, potassium, and lithium. The halo and halosubstituted anions can be chloro, bromo, or iodo. The solution can be used to treat paper, cardboard, and cellulosic materials generally, but for convenience, the disclosure describes the treatment of wood.

Aluminum halohydrates which can be employed include aluminum chlorohydrate, aluminum iodohydrate, and aluminum bromohydrate.

Exemplary of suitable water soluble salts are:
Zinc Acetate.$2H_2O$
Zinc Propionate
Manganese (+2) Acetate.$4H_2O$
Barium Acetate
Calcium Acetate
Calcium Iodoacetale
Calcium 2-Chloropropionate
Calcium 3-Chloropropionate
Calcium Isobutyrate
Calcium Acrylate
Lithium Acetate.$2H_2O$
Calcium Butyrate
Calcium Propionate
Calcium Formate
Cobaltous (+2) Acetate.$4H_2O$
Magnesium Acetate.$4H_2O$
Nickel (+2) Acetate.$4H_2O$
Cupric Acetate.$H_2O$
Lead (+2) Acetate.$3H_2O$
Mercuric (+2) Nitrate, and
Sodium Acetate.$3H_2O$
Suitable but somewhat less effective than the preceding are:
Zinc Nitrate.$6H_2O$
Magnesium Nitrate.$6H_2O$
Chromic (+3) Acetate.$H_2O$
Cupric Nitrate.$3H_2O$
Zinc Chloride
Zinc Sulfamate
Calcium Chloroacetate
Cadmium Bromide.$4H_2O$
Calcium Chloride.$2H_2O$ and
Potassium Iodide

DETAILED DESCRIPTION OF THE INVENTION

The non-aluminum metal salts can be prepared by reacting a mono, di, or trivalent oxide with the appropriate acid. Thus, zinc propionate is made by reacting zinc oxide with propionic acid.

The aluminum halohydrates useful in the invention can be represented by the formula: $Al_x(OH)_yX_z$, wherein X is a halogen such as chlorine, bromine, or iodine and x and y are integers of from 1 to 4 and z is an integer of from 5 to 1. The aluminum halohydrates are usually polymeric in nature and thus the above formula should not be considered restrictive. Typical non-limiting examples of the aluminum halohydrates that can be used in the present invention are: $Al_3OH_5Cl_4$, $Al_4OH_{10}Cl_2$, $Al_4OH_9Cl_3$, and $Al_2OH_4Cl_2$. Inasmuch as sulfate ion will precipitate the aluminum halohydrate, the solution should be substantially free of sulfate.

Any method of treating wood with aqueous treating solutions can be used when wood is treated with the aqueous wood-treating solutions of the present invention. These methods include treating wood by injection of the aqueous wood-treating solution under pressure in closed vessels or dipping in open vessels or by brush or spray painting of the solution. Also, in the method of treating wood with the aqueous wood treating solution of the present invention, the wood may be end-sealed in any manner known to those skilled in the art to enhance the water repellent effect of the aqueous wood-treating solution.

In accordance with the invention, combination fungicide and water repellent solutions can be made by selecting a fungicide as the water soluble salt. Fungicides suitable for use as the water soluble salt can be formed from one of the aforesaid anions and a cation selected from copper, zinc, barium, lithium, sodium, lead, mercury, cadmium, calcium, and potassium. Typical fungicides which can be employed as the water soluble salt include: cadmium formate, cadmium acetate, cadmium propionate, cadmium isobutyrate, cadmium butyrate, cadmium acrylate, cadmium nitrate, cadmium sulfamate, cadmium chloride, cadmium bromide, cadmium iodide, cadmium iodacetate, cadmium chloroacetate, cadmium 2-chloropropionate, cadmium 3-chloropropionate, cupric formate, cupric acetate, cupric propionate, cupric isobutyrate, cupric butyrate, cupric acrylate, cupric nitrate, cupric sulfamate, cupric chloride, cupric bromide, cupric iodide, barium formate, barium acetate, barium propionate, barium isobutyrate, barium butyrate, barium acrylate, barium nitrate, barium sulfamate, barium chloride, barium bromide, barium iodide, barium iodoacetate, barium chloroacetate, barium 2-chloropropionate, barium 3-chloropropionate, zinc formate, zinc acetate, zinc propionate, zinc isobutyrate, zinc butyrate, zinc acrylate, zinc nitrate, zinc sulfamate, zinc chloride, zinc bromide, zinc iodide, zinc iodoacetate, zinc chloroacetate, zinc 2-chloropropionate, zinc 3-chloropropionate, lithium formate, lithium acetate, lithium propionate, lithium isobutyrate, lithium butyrate, lithium acrylate, lithium iodide, lithium iodoacetate, lithium chloroacetate, lithium 2-chloropropionate, lithium 3-chloropropionate, sodium formate, sodium acetate, sodium propionate, sodium isobutyrate, sodium butyrate, sodium acrylate, sodium iodide, sodium iodoacetate, sodium chloroacetate, sodium 2-chloropropionate, sodium 3-chloropropionate, potassium formate, potassium acetate, potassium propionate, potassium isobutyrate, potassium butyrate, potassium acrylate, potassium iodide, potassium iodoacetate, potassium chloroacetate, potassium 2-chloropropionate, potassium 3-chloropropionate, calcium formate, calcium acetate, calcium propionate, calcium isobutyrate, calcium butyrate, calcium acrylate, calcium iodide, calcium iodoacetate, calcium chloroacetate, calcium 2-chloropropionate, calcium 3-chloropropionate, mercury +2 acetate or nitrate with aluminum chlorohydrates and lead acetate.

Although the amount of aluminum halohydrate and water soluble salt employed will depend upon the particular materials employed, a treating solution will generally contain from about 0.05 to about 2.0% aluminum halohydrate and from about 0.06 to about 4.0% water soluble salt. A concentrate will generally contain either powder or a solution of the more water soluble salts in an amount of from about 5 to 36% aluminum halohydrate and about 10% to 18% water soluble salt.

The following description is directed to several alternative embodiments of the aqueous wood-treating solution of the present invention. In these embodiments the aluminum halohydrate used is aluminum chlorohydrate in a 50 percent aqueous solution. Non-limiting examples of such solutions that are commercially available are Wickenol 303 solution, Wickenol 305 solution, and Wickenol 306 solution, all available as solutions or powders from Wickhen Products, Inc., Huguenot, New York. The Wickenol 303 solution is an aqueous 50 percent aluminum chlorohydrate which has an atomic ratio of two aluminum atoms to one chlorine atom, Wichenol 305 is the dichlorohydrate and Wickenol 306 the sesquichlorohydrate. For non-drug use, Wickenol 303 is now known as Wicklor 904—Al complex 56, Wicklor 305 is now known as Wicklor 906—Al complex 23, and Wickenol 306 is now known as Wicklor 905—Al complex 34. Other products which have ratios of one aluminum atom to one chlorine and intermediate ratios between one and two aluminum atoms to one chlorine atom may also be used. The diluted Wickenol solutions did not appear to exhibit high inherent water repellency when applied to wood by itself, but when used in the aqueous wood-treating solutions of the present invention a synergistic effect is obtained, resulting in an increased water repellency in treated wood.

The following examples will serve to illustrate preferred embodiments of the invention. All parts and percentages in said examples and elsewhere in the specification and claims are by weight unless otherwise specified.

EXAMPLES

The following stable concentrates which can be diluted to clear solutions were prepared by diluting the ingredients with water before mixing as the use of concentrated solutions tends to inhibit the solubilization of the components.

| Ingredients | Percent by Weight | | |
|---|---|---|---|
| Zinc Propionate | 14.0 | — | — |
| Zinc Acetate . 2H$_2$O | — | 20.3 | 20.3 |
| Wickenol 303* | 22.5 | 32.4 | — |
| Wickenol 306 | — | — | 32.4 |
| Deionized Water | 63.5 | 47.3 | 47.3 |
| Total Weight Percent | 100.0 | 100.0 | 100.0 |

*Wickenol is a trade name for aluminum chlorohydrate.

The above solutions were diluted with water to one percent zinc metal content and tested for inhibition of *ceratocystis piliferia* (a common sapstain fungus) mixed with mold growth and spores from wet infected pine sapwood. Small, clear, dry southern pine sapwood specimens were vacuum treated with an aqueous suspension of the mold and sapstain spores to a very high moisture content and dipped into the above described dilutions. After one week at room temperature and 100 percent relative humidity, the untreated controls were heavily sapstained but none of the treated specimens were attacked. The incubation period was continued for a total of three weeks with no sapstain attack on the treated specimens. The test was repeated using the first two solutions diluted to a 0.06 percent zinc metal content and there was no evidence of sapstain growth after 37 days. A solution of zinc acetate, 2H$_2$O alone at 0.21% had no fungicidal effect against sapstain.

Freshly planed dry southern pine sapwood boards containing over 50% springwood on the area to be tested were treated with test solutions by depositing a few drops of the solution on the wood and spreading with a sponge. The treated boards were dried for 24 hours at ambient temperature and allowed to sit for a week. The resultant boards were treated with 4 drops of water on both treated and untreated portions of the boards with a medicine dropper. The number of drops remaining on the boards was recorded after 15 minutes, 30 minutes, 1 hour, and 1½ hours, as a measure of the board's water repellency. The data obtained is reported in the following table.

| AQUEOUS TREATING SOLUTION | | | NUMBER OF WATER DROPS REMAINING FROM THE FOUR APPLIED | | | |
|---|---|---|---|---|---|---|
| Metal Salt at 1.0% By Weight | Wickenols At 1.6% By Weight | Soln. PH | 15 Min. | 30 Min. | 1 Hour | 1.5 Hours |
| Barium Acetate | None | 7.5 | 0 | 0 | | |
| Barium Acetate | W-306 | 5.3 | 4 | 4 | 2 | 2 |
| Barium Acetate | W-303 | 6.0 | 4 | 4 | 4 | 2 |
| Barium Acetate | W-305 | 4.9 | 4 | 4 | 4 | 4 |
| Calcium Acrylate | None | | 0 | 0 | | |
| Calcium Acrylate | W-303 | 5.9 | 4 | 4 | 4 | 4 |
| Ca Iodoacetate | W-303 | 4.7 | 4 | 4 | 4 | 3 |
| Ca Isobutyrate | W-303 | 5.5 | 4 | 4 | 4 | 3 |
| Ca 2-CL Propionate | W-303 | 5.6 | 4 | 4 | 4 | 3 |
| Ca 3-CL Propionate | W-303 | 4.6 | 4 | 4 | 4 | 3 |
| Ca Chloroacetate | W-303 | 4.2 | 4 | 4 | 2 | 1 |
| Zinc Acetate.2H$_2$O | None | 6.9 | 0 | 0 | | |
| Zinc Acetate.2H$_2$O | W-306 | 5.3 | 4 | 4 | 3 | 2 |
| Zinc Acetate.2H$_2$O | W-303 | 5.7 | 4 | 4 | 4 | 3 |
| Zinc Acetate.2H$_2$O | W-305 | 5.0 | 4 | 4 | 4 | 4 |
| Zinc Propionate | None | 6.2 | 0 | 0 | | |
| Zinc Propionate | W-306 | 5.3 | 4 | 4 | 4 | 4 |
| Zinc Propionate | W-303 | 5.6 | 4 | 4 | 4 | 4 |
| Zinc Propionate | W-305 | 5.0 | 4 | 4 | 4 | 4 |
| Calcium Acetate | None | 6.7 | 0 | 0 | | |
| Calcium Acetate | W-306 | 5.5 | 4 | 4 | 4 | 4 |
| Calcium Acetate | W-303 | 6.1 | 4 | 4 | 4 | 4 |
| Calcium Acetate | W-305 | 5.1 | 4 | 4 | 4 | 4 |
| Sodium Acetate.3H$_2$O | None | 7.9 | 0 | 0 | | |
| Sodium Acetate.3H$_2$O | W-306 | 5.4 | 4 | 4 | 4 | 4 |
| Sodium Acetate.3H$_2$O | W-303 | 5.5 | 4 | 4 | 4 | 4 |
| Sodium Acetate.3H$_2$O | W-305 | 5.0 | 4 | 4 | 4 | 4 |
| Lithium Acetate.2H$_2$O | W-306 | 5.5 | 4 | 4 | 4 | 4 |
| Magesium Acetate.4H$_2$O | W-306 | 5.6 | 4 | 4 | 4 | 4 |
| NONE | W-303 | 5.1 | 4 | 0 | | |
| NONE | W-306 | 4.4 | 4 | 0 | | |
| NONE | W-305 | 4.2 | 4 | 0 | | |

The following data tends to show a synergistic effect for the two salts. The specimens were tested for water repellancy three weeks after applying the treating solutions.

| Weight Percent Metal Salt in Solution | Weight Percent Wickenols Used | Number of Distilled Water Drops Remaining From the 4 Applied After | | | |
|---|---|---|---|---|---|
| | | 30 Min. | 1 Hour | 1.5 Hours | 2 Hours |
| 2% Sodium Acetate, 3H$_2$O | None | 0 | 0 | 0 | |
| 1% Sodium Acetate | 1.6 W-303 | 4 | 4 | 1 | 0 |
| 2% Barium Acetate | None | 0 | 0 | 0 | 0 |
| 1% Barium Acetate | 1.6 W-305 | 4 | 4 | 1 | 0 |
| 2% Zinc Acetate, 2H$_2$O | None | 4 | 0 | 0 | 0 |
| 1% Zinc Acetate, 2H$_2$O | 1.6 W-303 | 4 | 4 | 4 | 0 |
| 2% Zinc Propionate | None | 4 | 0 | 0 | 0 |
| 1% Zinc Propionate | 1.6 W-303 | 4 | 4 | 4 | 0 |
| 2% Calcium Formate | None | 0 | 0 | 0 | |
| 1% Calcium Formate | 1.6 W-305 | 4 | 2 | 1 | 0 |
| 2% Calcium Acetate | None | 0 | 0 | 0 | |
| 1% Calcium Acetate | 1.6 W-303 | 4 | 4 | 3 | 1 |
| None | 3.2 W-303 | 2 | 1 | 1 | 0 |
| None | 3.2 W-306 | 1 | 0 | 0 | 0 |
| None | 3.2 W-305 | 0 | 0 | 0 | |
| Untreated Wood | | 0 | | | |

It was found that high temperature drying of the treated wood decreases its water repellency, accordingly, temperatures should be kept as low as possible or less than about 160° F. dry bulb temperature to a moisture content of 25%.

If clear solutions are desired so that the cellulose product is not discolored, then the copper, nickel and chromium salts should be avoided as these salts discolor the wood whereas the other salts do not.

Further, in formulating barium solutions it was necessary to employ distilled water because the barium salts react with the small amounts of sulfate ion found in most tap water.

While the invention has been illustrated by specific examples, the other compounds enumerated in the disclosure are found to have water repellency effectiveness when used to treat cellulosic materials, and may have fungicidal effectiveness.

What is claimed:

1. A method for controlling fungi consisting essentially of treating said fungi with a fungicidal amount of an aluminum halohydrate wherein the halogen is selected from chlorine, bromine and iodine and a water soluble salt of a mono or divalent cation selected from copper, zinc, barium, lithium, lead, mercury, cadmium, calcium, sodium, and potassium, and a monovalent anion selected from formate, acetate, haloacetate, acrylate, methacrylate, propionate, chloro and bromo-propionate, butyrate, isobutyrate, nitrate, sulfamate, iodide, bromide, and chloride, said water soluble salt excluding the sulfamates, nitrates, chlorides and bromides of sodium, potassium, lithium and calcium.

2. A method for increasing the water repellency of wood consisting essentially of treating the wood with an aqueous solution comprising an effective amount of a mixture of aluminum halohydrate wherein the halogen is selected from chlorine, bromine and iodine and a water soluble salt of a mono, di or trivalent cation selected from zinc, manganese, barium, calcium, cobalt, magnesium, nickel, copper, cadmium, strontium, beryllium, lead, mercury, chromium, sodium, lithium, and potassium and a monovalent anion selected from formate, acetate, haloacetate, acrylate, methacrylate, propionate, chloro and bromo-propionate, butyrate, isobutyrate, nitrate, sulfamate, iodide, bromide, and chloride, said water soluble salt excluding the nitrates, sulfamates, chlorides and bromides of sodium, potassium and lithium.

* * * * *